(12) United States Patent
Olesen

(10) Patent No.: US 9,250,176 B2
(45) Date of Patent: Feb. 2, 2016

(54) FLEXIBLE SAMPLE CONTAINER

(75) Inventor: Tom Olesen, Gørløse (DK)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 330 days.

(21) Appl. No.: 13/582,593

(22) PCT Filed: Mar. 2, 2011

(86) PCT No.: PCT/DK2011/050064
§ 371 (c)(1),
(2), (4) Date: Sep. 4, 2012

(87) PCT Pub. No.: WO2011/107102
PCT Pub. Date: Sep. 9, 2011

(65) Prior Publication Data
US 2012/0327404 A1    Dec. 27, 2012

Related U.S. Application Data

(60) Provisional application No. 61/310,499, filed on Mar. 4, 2010.

(30) Foreign Application Priority Data

Mar. 4, 2010 (DK) .............................. PA 2010 0170

(51) Int. Cl.
*G01N 1/10* (2006.01)
*G01N 21/01* (2006.01)
(Continued)

(52) U.S. Cl.
CPC ............... *G01N 21/05* (2013.01); *B01L 3/505* (2013.01); *G01N 21/85* (2013.01);
(Continued)

(58) Field of Classification Search
CPC ............. G01N 21/85; G01N 21/8557; G01N 15/1463; A61M 5/365
USPC .................. 356/244, 246, 432–440, 335–343
See application file for complete search history.

(56) References Cited

U.S. PATENT DOCUMENTS 3,814,522 A    6/1974    Clark et al.
3,921,622 A    11/1975    Cole
(Continued)

FOREIGN PATENT DOCUMENTS

CN            101322145 A    12/2008
DE    10 2008 000 504 A1    9/2009
(Continued)

OTHER PUBLICATIONS

International Search Report (Form PCT/ISA/210) mailed in International Application No. PCT/DK2009/050321 A1 Jan. 14, 2010, 3 sheets, Nordic Patent Institute, Taastrup, DK.
(Continued)

*Primary Examiner* — Tarifur Chowdhury
*Assistant Examiner* — Sunghee Y Gray

(57) ABSTRACT

The invention relates to a system for holding a fluid sample, said system comprising a transparent flexible tube for holding said fluid sample, a tube holder for holding said tube, a first flattening element, and second flattening element, wherein said first flattening element and said second flattening element may be moved relative to each other thereby changing said transparent flexible tube from a first state to a second state, where at least a first cross sectional dimension of said tube is smaller in said second state than in said first state.

15 Claims, 4 Drawing Sheets

Figure 1:
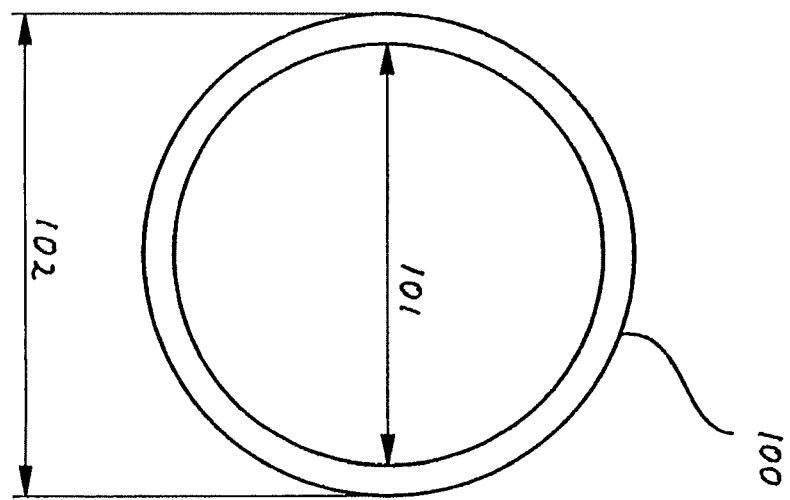
Figure 1:
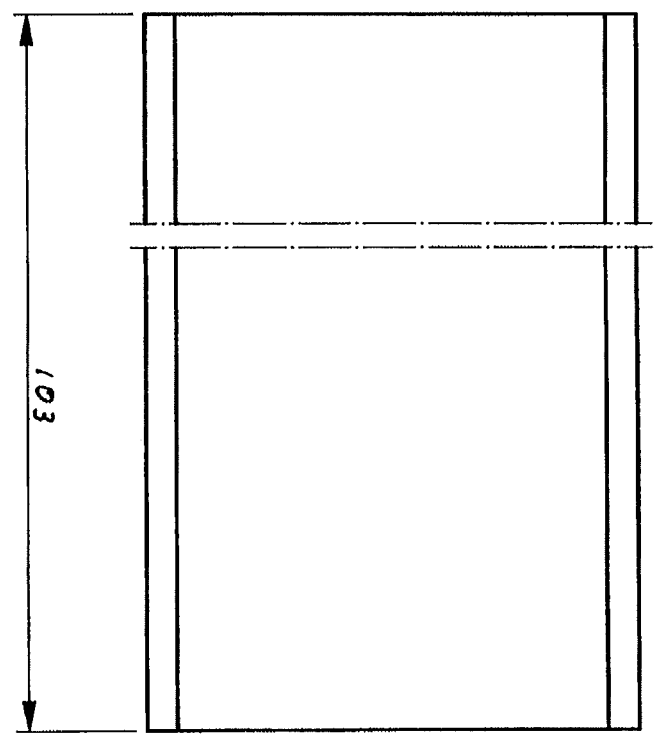

(51) Int. Cl.
*G01N 21/00* (2006.01)
*G01N 15/02* (2006.01)
*G01N 21/05* (2006.01)
*B01L 3/00* (2006.01)
*G01N 21/85* (2006.01)
*G01N 21/03* (2006.01)

(52) U.S. Cl.
CPC . *B01L 2300/0832* (2013.01); *B01L 2300/0877* (2013.01); *B01L 2400/0487* (2013.01); *B01L 2400/0655* (2013.01); *G01N 2021/0346* (2013.01); *G01N 2021/0364* (2013.01); *G01N 2021/8557* (2013.01)

(56) References Cited

U.S. PATENT DOCUMENTS

| | | | |
|---|---|---|---|
| 4,448,534 A | 5/1984 | Wertz et al. | |
| 5,102,392 A | 4/1992 | Sakai et al. | |
| 5,123,275 A | 6/1992 | Daoud et al. | |
| 5,329,461 A | 7/1994 | Allen et al. | |
| 5,393,494 A | 2/1995 | Greenfield et al. | |
| 5,488,567 A | 1/1996 | Allen et al. | |
| 5,649,032 A | 7/1997 | Burt et al. | |
| 5,672,887 A | 9/1997 | Shaw et al. | |
| 5,672,888 A | 9/1997 | Nakamura | |
| 5,690,895 A | 11/1997 | Matsumoto et al. | |
| 5,939,709 A | 8/1999 | Ghislain et al. | |
| 6,153,400 A | 11/2000 | Matsumura et al. | |
| 6,160,908 A | 12/2000 | Hakozaki | |
| 6,313,452 B1 | 11/2001 | Paragano et al. | |
| 6,656,683 B1 | 12/2003 | Reuben et al. | |
| 6,867,851 B2 | 3/2005 | Blumenfeld et al. | |
| 6,869,570 B2 | 3/2005 | Wardlaw | |
| 6,873,725 B2 | 3/2005 | Xu | |
| 6,919,960 B2 | 7/2005 | Hansen et al. | |
| 7,058,233 B2 | 6/2006 | Silber | |
| 7,068,365 B2 | 6/2006 | Hansen et al. | |
| 7,194,118 B1 | 3/2007 | Harris et al. | |
| 7,576,307 B2 | 8/2009 | Yazdanfar et al. | |
| 7,630,628 B2 | 12/2009 | Ogihara | |
| 7,634,128 B2 | 12/2009 | Snow et al. | |
| 7,634,129 B2 | 12/2009 | Strom | |
| 7,764,821 B2 | 7/2010 | Coumans et al. | |
| 7,860,302 B2 | 12/2010 | Sato et al. | |
| 7,949,161 B2 | 5/2011 | Kawanabe et al. | |
| 2002/0154216 A1 | 10/2002 | Yahiro | |
| 2002/0155487 A1 | 10/2002 | Greenberger | |
| 2003/0059866 A1 | 3/2003 | Lewis et al. | |
| 2003/0103277 A1 | 6/2003 | Mohwinkel | |
| 2003/0138139 A1 | 7/2003 | Strom | |
| 2003/0151735 A1 | 8/2003 | Blumenfeld et al. | |
| 2004/0008867 A1 | 1/2004 | Fein | |
| 2005/0068614 A1 | 3/2005 | Yoneyama et al. | |
| 2005/0148085 A1 | 7/2005 | Larsen | |
| 2005/0179899 A1 | 8/2005 | Palti-Wasserman et al. | |
| 2005/0259437 A1 | 11/2005 | Klein et al. | |
| 2006/0084125 A1 | 4/2006 | Laor | |
| 2007/0009395 A1 | 1/2007 | Jiang | |
| 2007/0087442 A1 | 4/2007 | Wardlaw | |
| 2007/0122143 A1 | 5/2007 | Okamoto | |
| 2008/0011060 A1 | 1/2008 | Lynnworth | |
| 2008/0019584 A1* | 1/2008 | Lindberg et al. | 382/134 |
| 2008/0100703 A1 | 5/2008 | Yamada | |
| 2008/0192128 A1 | 8/2008 | Kempe et al. | |
| 2008/0246946 A1 | 10/2008 | Hansen et al. | |
| 2009/0021260 A1 | 1/2009 | Stringer | |
| 2009/0059362 A1 | 3/2009 | Jansen | |
| 2009/0078047 A1* | 3/2009 | Dam | 73/606 |
| 2009/0231689 A1 | 9/2009 | Pittsyn et al. | |
| 2009/0239250 A1 | 9/2009 | Klug et al. | |
| 2009/0295963 A1 | 12/2009 | Bamford et al. | |
| 2010/0106082 A1* | 4/2010 | Zhou | 604/67 |
| 2010/0208263 A1 | 8/2010 | Stevens et al. | |
| 2010/0314533 A1 | 12/2010 | Stallinga et al. | |
| 2011/0261164 A1 | 10/2011 | Olesen | |
| 2012/0244519 A1 | 9/2012 | Olesen | |
| 2013/0023041 A1 | 1/2013 | Greenberger et al. | |

FOREIGN PATENT DOCUMENTS

| | | | | |
|---|---|---|---|---|
| GB | 2 182 432 A | 5/1987 | | |
| JP | 08-502347 A | 3/1996 | | |
| JP | 2003-065952 A | 3/2003 | | |
| JP | 2003-161691 A | 6/2003 | | |
| JP | 2003161691 | * 6/2003 | | G01N 15/14 |
| JP | 2006-234663 A | 9/2006 | | |
| JP | 2007-322685 A | 12/2007 | | |
| RU | 2232988 | 7/2004 | | |
| WO | 89/01796 A1 | 3/1989 | | |
| WO | 93/24213 A1 | 12/1993 | | |
| WO | 98/56441 A1 | 12/1998 | | |
| WO | 02/055137 A2 | 7/2002 | | |
| WO | 02/075284 A2 | 9/2002 | | |
| WO | 02/084256 A1 | 10/2002 | | |
| WO | 2006013312 A1 | 2/2006 | | |
| WO | 2007/036305 A1 | 4/2007 | | |
| WO | 2007/047908 A2 | 4/2007 | | |
| WO | 2008/010761 A1 | 1/2008 | | |
| WO | 2008/134678 A1 | 11/2008 | | |

OTHER PUBLICATIONS

Written Opinion of the International Search Authority (Form PCT/ISA/237) mailed in International Application No. PCT/DK2009/050321 Jan. 14, 2010, 6 pages, Nordic Patent Institute, Taastrup, DK.

International Search Report dated Mar. 23, 2011, issued in corresponding International Application No. PCT/DK2010/050327 (3 pages).

International Search Report dated Feb. 28, 2011, issued in corresponding International Application No. PCT/DK2011/050064 (4 pages).

Decision on Grant issued in corresponding Russian Patent Application No. 2011127424/28(040583), dated Apr. 22, 2014, and translation thereof.

Office Action (Notification of Reasons for Rejection) issued on Sep. 24, 2014, by the Japan Patent Office in corresponding Japanese Patent Application No. 2012-555295 and an English Translation of the Office Action. (8 pages).

An English-language translation of the First Office Action issued on Jun. 4, 2014, by the State Intellectual Property Office of the People's Republic of China in corresponding Chinese Patent Application No. 201180012265.8. (9 pages).

The extended European Search Report issued on Jun. 16, 2014, by the European Patent Office in corresponding European Patent Application No. 11750218.7-1554. (7 pages).

* cited by examiner

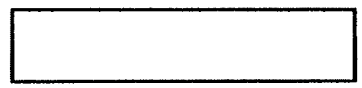
FIG 3A
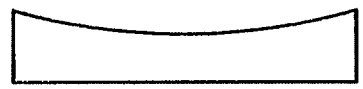
FIG 3B
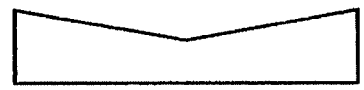
FIG 3C
FIG 3D
FIG 3E
FIG 3

FLEXIBLE SAMPLE CONTAINER

The present invention relates to a flexible sample container to be used in connection to measuring on fluid samples. The system is suitable for measuring on both large and small quantities of sample fluid, such as in connection to samples comprised of a few micro liters.

In U.S. Pat. No. 3,814,522 Clark and Wells disclose a tube and method for using the tube in analysis of urine samples. The tube is made of glass, plastic or other un-flexible transparent material and comprises a circular upper end and a flattened lower end providing two substantially parallel surfaces. The lower end is suitable for use in a microscope for examination of sediments in the flattened portion. The tube is suitable for use together with a centrifuge for concentration of the sediments in the flattened portion.

The suggested tube provides a simple way of applying a sample to a sample holder to be inserted into a microscope for examination of the sample. However, the suggested tube is to be filled using a pipette or similar and after centrifugation and sedimentation the surplus fluid is to be disposed before incision into a microscope. This indicates that the fluid, e.g. urine, is to be manually handled at least two times, exposing the handler for possible diseases and the sample for contamination. Further, the tube is to be inserted into the microscope by hand, making automatic replacement of a tube difficult or impossible.

In U.S. Pat. No. 5,672,888 Shaw et al. disclose an optical bubble detector comprising an optics block formed with a V-shaped recess, and a clamp block. The optics block and clamp block cooperatively press or "sandwich" the flexible tubing into the V-shaped recess and deform it into a triangular prismatic cross-section. A generally U-shaped optical interrupter element, containing a photo emitter and a photo sensor, fits into the optics block in such a manner that a light beam is directed radially into the triangular tubing section. The clamp block "windows" the transmitted and received light from the optical interrupter, to allow only a thin channel of light to be transmitted; this minimizes optical noise during measurement. The optical bubble detector is utilized for detecting bubbles in e.g. saline solutions, and there is no imaging of the fluid in the tube during measurement.

In WO/2006/013312 Chu disclose a fluid detector and alarm system. The invention relates to a fluid detector and in particular to such a system for detecting the presence of a first fluid phase within an administrative system for a second fluid phase. Most particularly, the invention relates to such a system for detecting the presence of air in a liquid administrative system such as those used in the intravenous infusion of fluid in critically ill patients, or to such a system for detecting the presence of liquid within an air-filled system, and for triggering an alarm if air or liquid is inadvertently present in the system.

Also in WO 2002/084256 an optical bubble detector is disclosed comprising an emitter and a photo detector. The sample cell and the optical sensor use light refraction to determine the presence and size of a bubble passing through the sample cell.

Further, in WO 1989/001796 a bubble detector is disclosed. In order to detect bubbles in a fluid flowing along a passageway, a portion of the passageway is formed with an elongate cross-section having parallel longer side walls. A first light path passes across the passageway portion and a second light path not passing across the passageway is provided as a reference. When a bubble bigger than the gap between the side walls of the passageway portion passes into the passageway portion, the amount of light passing along the first light path increases and, if the ratio of light passing along the first light path to light passing along the second, reference light path exceeds a predetermined value, a bubble is deemed to have been detected.

In none of the aforementioned disclosures an optical scanning apparatus is utilized to image the fluid within the tube.

The present invention provides a system and a method for overcoming at least one of the drawbacks of the tubes as disclosed in the prior art. Specifically, one object of the present invention is to provide a system for holding a fluid sample which is preferably simple to use. The system comprises a transparent flexible tube for holding the fluid sample and a tube holder for holding the tube. Further, the system comprises a first flattening element and a second flattening element, wherein the first flattening element and the second flattening element may be moved relative to each other thereby changing the transparent flexible tube from a first state to a second state, where at least a first cross sectional dimension of the tube is smaller in the second state than in the first state.

A second object of the present invention is to provide a method for providing a fluid sample to an optical scanning apparatus which preferably results in a high quality of images obtained by scanning and preferably in a fast and simple manner. The method comprises arranging a flexible tube in a tube holder and arranging the tube holder in relation to the optical scanning apparatus. The method further comprises providing the fluid to the flexible tube, and moving a first flattening element and a second flattening element relative to each other thereby changing the transparent flexible tube from a first state to a second state, where at least a first cross sectional dimension of the tube is smaller in the second state than in the first state.

One or more of these objects have been solved by the invention and embodiments thereof as defined in the claims and as described below.

In the context of the present application, the phrase "flexible" is used to describe one aspect of the physical nature of a tube. A flexible tube may be temporarily deformed by bending, stretching, flattening, compressing, etc, without breaking or leaking, and when released from deformation, the flexible tube substantially returns to the shape it had before being deformed. A flexible tube may be made of Silicone or similar material.

In the context of the present application the phrase "flexible tube" and "tube" and "sample container" may be used for denoting the same part. In the first state, the cross section of the tube may be substantially circular shaped or it may be substantially oval or similar shaped.

In the field of optics, transparency is the physical property of allowing light to pass through a material substantially without being modified. It is preferred that the flexible tube utilized in the present invention is made of a substantial transparent material or comprises a transparent window.

In the context of the present application, the phrase "fluid" is used to describe a substance having a viscosity sufficiently low for enabling it to float or being pumped into or through a tube. A fluid may comprise water, urine, blood, milk and similar liquids or substances as well as solutions comprising them. Cited from wordnetweb.princeton.edu: "A fluid is a continuous amorphous matter that tends to flow and to conform to the outline of its container".

A clamp should in the present invention be understood as a device which may be used for blocking the flow of a fluid in a vessel or tube by pressing the walls of the tube together, such as a hemostatic clamp.

In the context of the present application, the phrase "substantially at stand still" refers to a situation, wherein the movement of the particles in an inhomogeneous liquid sample does not affect the determination of the parameters of the sample, such as the parameters of particles in the sample. In one embodiment, substantially at stand still refers to the situation where the movement of the particles in the period of time lapsed in between the acquisition of two adjacent images in a sequence of spatially displaced images should be substantially smaller than the distance between these two adjacent images, such as one tenth of the distance. In one embodiment, substantially at stand still refers to the situation where there is no mass flow of said liquid sample during the acquisition of at least a part of said plurality of images. In one embodiment for imaging cells and their content, the movement of the cell may be limited to an extent whereby sufficiently sharp images of the cell can be obtained so that details relating to e.g. the nuclei can be determined. In embodiments adapted for determining parameters relating to cells, the term "substantially at stand still" thus may mean that the movement of said cells during the acquisition of an image may be limited to the Depth of Field (DOF) or a fraction of DOF, such as one thousandth of the (DOF), such as one hundredth of the DOF, such as one tenth of the DOF, such as one fifth of the DOF, such as one third of the DOF. The DOF may be in the range 0.1 micrometer to 200 micrometers. The movement of the particles in the liquid sample at stand still conditions may hence be less than 0.001 micrometer per second, such as less than 0.01 micrometer per second, as less than 0.1 micrometer per second, such as less than 1 micrometer per second. The particle parameter may in this embodiment be the number and size of nuclei or the distance between the nuclei in a cell. In one embodiment where the details of the particle are of less interest, such as for counting particles, the limitation on the particle movement is such that the counting of the particles is not influenced by the movement. The movement of the particles to be counted may hence be less than 0.01 micrometer per second, such as less than 0.1 micrometer per second, such as less than 1 micrometer per second, such as less than 10 micrometer per second, such as less than 100 micrometer per second, such as less than 1 millimeter per second.

In one embodiment the system further comprise an optical scanning apparatus for acquiring at least one image from the fluid sample in the transparent flexible tube in the first state and/or in the second state, wherein the fluid sample is at stand still.

In one embodiment the system the optical scanning apparatus is adapted to calculate a parameter relating to the fluid sample and from the parameter determine a new state for the flexible tube.

In one embodiment, the transparent flexible tube in the first state has an inner diameter less than about 25 mm, such as less than about 20 mm, such as less than about 15 mm, such as less than about 10 mm, such as less than about 5 mm, such as less than about 3 mm, such as less than about 2 mm, such as less than about 1.5 mm, such as less than about 1 mm.

In one embodiment, the flexible tube comprises an inlet for introducing a fluid into the tube. The inlet may be connected to a hose or other type of outlet, or work as a drain to a pipe or catheter or similar.

In one embodiment, the flexible tube comprises an outlet utilized to remove the fluid present in the tube. The outlet may work as a drain, directing the fluid directly to a waste container or similar, In one embodiment, the flexible tube comprises both an inlet and an outlet. The inlet and the outlet may both be connected to the same pipe or catheter. In this way, the tube works as a shunt to the pipe or catheter. The outlet may also work as a drain, directing the fluid directly to a waste container or similar.

In one embodiment, the system comprises a tube pump adapted to pump fluid into the tube via the inlet. If the tube inlet and tube outlet is connected to the same pipe or catheter it may be necessary to activate a tube pump for pumping fluid into the tube, or for removing fluid present in the tube and replacing the fluid with a new sample. Various types of tube pumps are generally known in the art, and it will be appreciated that any type of tube pump may be used in the system of the present invention. The tube pump may be activated electronically or manually.

In one embodiment, the system comprises at least a first clamp for clamping said tube. When the tube is clamped, the flow of the fluid through the tube is stopped. When the tube is un-clamped the fluid may flow freely in the tube. Various types of clamps are known in the art, and any type of clamp may be utilized in the system of the present invention as long as the clamping substantially stops the flow in the tube.

The flattening element may be comprised of any suitable material, such as metal or plastic. In one embodiment, at least one of the flattening elements comprises a substantially transparent region. The transparent region may be utilized for transmitting electromagnetic waves through the flattening element and a tube positioned between the flattening elements. The transparent region of the flattening element may be comprised of a substantially transparent material such as glass or transparent plastic.

In one embodiment, the transparent region of the flattening elements comprises an inner surface and an outer surface. The inner surface should be understood as being the surface facing the tube, while the outer surface is the surface at the opposite side of the flattening element. In one embodiment, the inner surface is substantially flat. In another embodiment the inner surface comprises a guiding groove. The guiding groove may be utilized to position the tube in a preferred position relating the optical path of the optical microscope. The guiding groove may be shaped as a "V", it may be shaped as an arc, or it may be shaped comprising a flat area in the middle and an elevated area in each side to form a border. A skilled person will appreciate that many different shapes may be used as a guiding groove, and the herein mentioned shapes should only be considered to be examples of these.

In one embodiment, the transparent region comprises at least one optical element. The optical element may be comprised of a lens, a wedge, a polarizer, an aperture, a color filter, a density and a grating. Other optical elements known in the art may also be utilized. The optical element comprised in the transparent region may form a part of the optical path of the optical microscope.

In one embodiment, the first flattening element and the second flattening element are moved relatively to each other by utilizing a stepper motor or by a piezo electric motor or similar. Indeed, a skilled person will appreciate, that any type of motor or actuator suitable for micro-mechanics may be used to move the flattening elements relatively to each other.

In one embodiment, the first flattening element and the second flattening element are moved relatively to each other is such a way that the distances between the rims of the elements are changed uniformly. In one embodiment, the distances between the rims of the elements are changed in such a way, that the change in distance is larger at a first rim area relative to a second rim area. This effect may also be accomplished using a flattening element shaped as a wedge. The wedge effect may be utilized in the longitudinal direction of the tube (along the tube length) and it may be utilized in the transversal direction of the tube (perpendicular to the tube length) as well as a combination thereof.

In one embodiment, the flattening element may have two or more steps. When utilized to flatten the flexible tube, each step may provide a different measurement volume. This may be utilized when using the flexible tube in connection with an optical scanning device for measuring at least two different parameters relating to the particles in the fluid. The parameters may e.g. be the number of platelets in blood and the number of white blood cells in the blood. For determining the number of platelets in blood, it is advantageous to have a thin measurement volume, while enumeration of white blood cells may advantageously be made in a relatively thicker measurement volume. Utilizing a flattening element comprising two steps, the parameters may be measured in one measurement.

In one embodiment, the shape of the tube in its second state is such that the distance between the inner wall of a part of the tube being in contact with the first flattening element to the inner wall of a part of the tube being in contact with the second flattening element is less than about 25 mm, such as less than about 20 mm, such as less than about 15 mm, such as less than about 10 mm, such as less than about 5 mm, such as less than about 3 mm, such as less than about 2 mm, such as less than about 1 mm, such as less than about 0.5 mm, such as less than about 0.25 mm, such as less than about 0.1 mm, such as less than about 0.05 mm.

The method of the present invention comprises providing a fluid sample to an optical microscope. The method comprises arranging a flexible tube in a tube holder and arranging the tube holder in relation to the optical microscope. The flexible tube may be arranged in the tube holder by attaching it to the tube holder, and the tube holder may be attached to the optical microscope. The method further comprises providing the fluid to the flexible tube, and moving a first flattening element and a second flattening element relative to each other thereby changing the transparent flexible tube from a first state to a second state where at least a first cross sectional dimension of said tube is smaller in the second state than in the first state.

An optical scanning apparatus to be used together with the flexible tube of the present invention may comprise an image acquisition device for acquiring images of the fluid sample comprised in the flexible tube. Further, there may be an image analyzing unit in connection to the optical scanning device and image acquisition device for analyzing images to determine at least one parameter describing particles comprised in the fluid. The parameters may comprise the enumeration of the particles, the concentration of the particles, the morphology of the particles, the turbidity of the fluid or the average size of the particles. Indeed a large number of parameters may be determined to characterize the fluid or the particles within fluid.

The optical scanning apparatus may be a common optical microscope comprising a digital camera or it may be a more specialized optical scanning apparatus dedicated to acquiring image stacks of fluids comprised in a sample container. In international patent application PCT/DK/2009/050321 filed by the same inventor as the present invention a scanning apparatus comprising an oblique scanning path is disclosed. This scanning apparatus is very well suited for being used in connection with the present invention.

The system and method of the present invention may be adapted to change the thickness of the tube after each image acquisition. When an image has been acquired and the image analysing device has been invoked to determine the parameter(s) describing the fluid and the contents thereof, the parameter(s) may be used for determining a new optimal tube thickness for the next measurement.

In one embodiment, the method further comprises acquiring at least one image from the optical microscope, determining at least one parameter relating to the fluid from the images, determining a new optimal tube thickness from the parameters and moving the first flattening element and the second flattening element relative to each other until the tube has been flattened to the new optimal tube thickness.

In one embodiment, the parameters relates to the concentration of particles in the fluid.

BRIEF DESCRIPTIONS OF THE DRAWINGS

Figure 2:
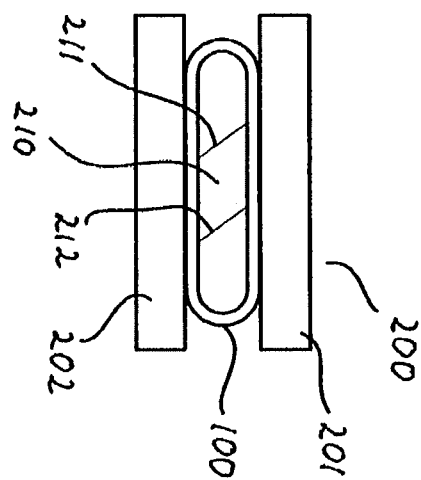
Figure 2:
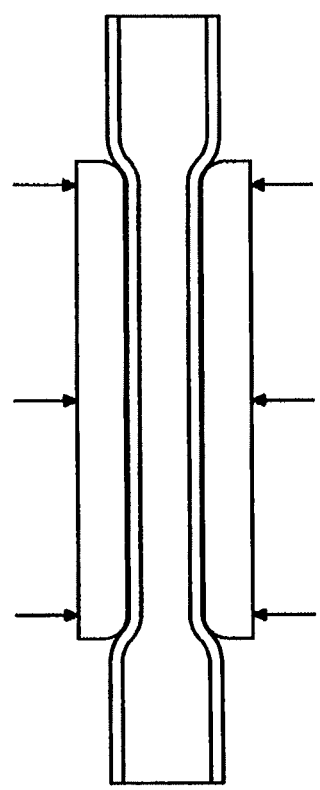
Figure 4:
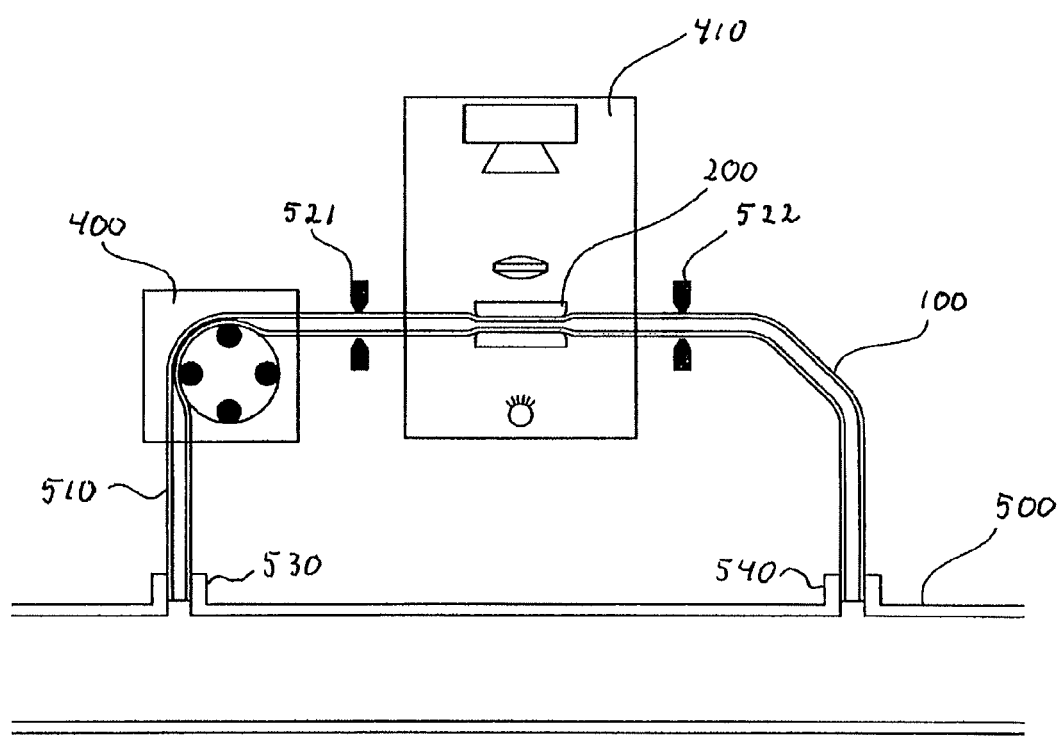

FIG. 1 shows a flexible tube,
FIG. 2 shows the flexible tube in compressed state,
FIG. 3 shows different version of a positioning grove,
FIG. 4 shows the flexible tube in connection with a water pipe The figures are schematic and may be simplified for clarity. Throughout, the same reference numerals are used for identical or corresponding parts.

FIG. 1 shows a flexible tube which may be used in a system according to the present invention. The tube has an outer diameter 102, an inner diameter 101 and a tube length 103. The tube may be made of a flexible material such as optical grade Silicone.

FIG. 2 shows the flexible tube 100 inserted into a flattening element 200 comprising a first flattening element 201 and a second flattening element 202. The two flattening elements are made of a transparent material such as glass. After the flexible tube 100 has been inserted into the flattening element 200, the two flattening elements 201 and 202 are pressed together to flatten the flexible tube 100. The flattening of the tube 100 changes the shape of the tube 100 from being circular to an oval-like shape with two parallel flat surfaces. A measurement volume 210 comprising first border 211 and second border 212 is defined within the flexible tube 100 between the two parallel surfaces. The distance between the two parallel flat surfaces depends on the force applied by the flattening element 200. The position of the first border 211 and the second border 212 do not depend on the distance between the parallel surfaces. The size of the measurement volume is therefore changed with the distance of the parallel surfaces. If the distance is small, the measurement volume 210 is small, and if the distance is large, the measurement volume 210 is correspondingly large. The measurement volume 210 may thus be adjusted to fit the desired measurement parameters.

In the embodiment illustrated in FIG. 2, the first flattening element 201 closest to the optical microscope is flat, but other shapes may also be utilized, such as a wedge or a lens. Also other optical elements may be included in the flattening element, such as a polarization filter, density filter or wavelength filter.

The second flattening element 202 may be flat, but may also have other shapes, such as in embodiments where the second flattening element is optically only used for illuminating the tube 100. In FIG. 3 different types of a flattening element 202 is shown. In FIG. 3A a standard flat flattening element 202 is shown, while in FIGS. 3B-3E flattening elements 202 comprising a positioning groove 203 is shown. In FIG. 3B a circular shaped positioning groove is shown. In FIG. 3C a V-shaped positioning groove is shown, while the positioning groove in FIG. 3D is formed as a recess in the flattening element 202. The purpose of the positioning groove is to help position the flattened tube exactly at the measurement position of the optical microscope. The positioning grove may be combined with an optical element, such as a lens, a wedge, a polarization filter, a density filter, a wavelength filter or an aperture as shown in FIG. 3E. The combination of a positioning groove and an optical element may be accomplished by selecting the inner wall of the flattening element to be a positioning groove and the outer wall to e.g. have a lens shape (concave or convex). Further, the material of which the flattening element is made may have a filter function.

In FIG. 4 the flexible tube 100 is shown in a setup for on-line monitoring of bacteria in tab-water. The setup comprises a pipe 500 comprising water from the water works. A shunt 510 comprising a flexible tube 100, a tube pump 400, a first clamp 521 and a second clamp 522, and a tube holder 410 comprising a flattening element 200 is connected to the pipe 500 via an inlet 530 and an outlet 540. The first clamp 521 is positioned upstream relative to the flattening element 200, while the second clamp 522 is positioned downstream relative to the flattening element 200. The first clamp 521 and/or the second clamp 522 may be positioned as close to the flattening element 200 as practical possible so that the volume within the tub between the two clamps is as small as possible. This will decrease the time for the fluid to stop flowing and being ready for measurement.

The tube pump 400 is activated to suck water at the inlet 530 from the pipe 500 through the flexile tube 100 and to the outlet 540. During operation of the tube pump, the first clamp 521 and the second clamp 522 should be opened. After activation of the tube pump 400 for a period of time, the tube 100 has been filled with water from the pipe 500, and the tube pump 400 is deactivated. It is preferred that the water in the tube 100 is at stand still during measurement, and to ensure this the first clamp 521 and the second clamp 522 is activated to stop the water in the tube to flow.

The flattening element 200 is now activated to flatten the flexible tube 100, until the required distance between the inner walls of the tube has been achieved. When this is accomplished, the measurement procedure is started. The measurement procedure may comprise an optical sectioning of the measurement volume.

For some applications, the flattening element may be activated before or during the activation of the pump. The flattening element may also be arranged to provide a substantially constant tube thickness during a procedure, wherein a plurality of measurements are performed.

During the measurement procedure, it may be determined that the distance between the inner walls of the tube should be changed to optimize the measurement procedure. If e.g. it is determined that the concentration of bacteria in the tab water is very low, a larger volume could be measured. The distance between the walls of the tube should therefore be large. If the concentration between two measurements starts to increase, it may be desired to decrease the measurement volume, to get a lower bacteria count. After changing the inner wall distance, the measurement procedure is continued.

After the measurement procedure has been completed, the water in the flexible tube 100 should be replaced with a new sample. This is done by first deactivating the flattening element 200 to release the tube from being flattened, then opening the clamps 521 and 522 and activating the tube pump 400. After a period of time, the water in the flexible tube 100 has been completely replaced with a new sample of water, and the tube pump 400 is be deactivated and the two clamps 521 and 522 is activated to stop the water flow through the flexible tube 100.

There are several different types of tube pumps. If the tube pump is if a type wherein the fluid is completely stopped from flowing when the pump is deactivated, the two clamps 521 and 522 may be omitted.

The outlet 540 from the flexible tube 100 may be connected to the same pipe as the inlet 530. In this case, the tube pump may be necessary for replacing the fluid sample in the flexible tube. If the outlet is connected to another pipe or a drain or similar, the tube pump may not be necessary, as the fluid pressure at the inlet compared to the fluid pressure at the outlet may be sufficiently higher to press a new sample into the tube replacing the existing one.

Some preferred embodiments have been shown in the foregoing, but it should be stressed that the invention is not limited to these, but may be embodied in other ways within the subject-matter defined in the following claims.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

All features of the inventions including ranges and preferred ranges can be combined in various ways within the scope of the invention, unless there is specific reasons for nor to combine such features.

The invention claimed is:

1. A system for holding a fluid sample, comprising:
a transparent flexible tube for holding said fluid sample,
a tube holder for holding said tube,
a first flattening element,
a second flattening element,
wherein at least one of said first flattening element and said second flattening element can be moved relative to each other, thereby changing said transparent flexible tube from a first state to a second state, wherein at least a first cross sectional dimension of said tube is smaller in said second state than in said first state,
an optical scanning apparatus comprising an image acquisition device for acquiring images of the fluid sample comprised in the flexible tube at least in the second state, and
a clamp for clamping said tube in order to maintain the fluid sample at a stand still while the image acquisition device acquires images of the fluid sample.

2. The system according to claim 1, wherein said optical scanning apparatus is adapted to calculate a parameter relating to said fluid sample and from said parameter determine an optimal degree of the first cross sectional dimension for said flexible tube based on the calculated parameter.

3. The system according to claim 1, wherein said transparent flexible tube in a first state has an inner diameter less than about 25 mm.

4. The system according to claim 1, wherein said flexible tube comprises an inlet and/or an outlet, and said system preferably further comprising a tube pump adapted to pump fluid into said tube via said inlet.

5. The system according to claim 1, wherein at least one of said flattening elements comprises a transparent region.

6. The system according to claim 5, wherein said transparent region comprises an inner surface and an outer surface.

7. The system according to claim 6, wherein said inner surface is substantially flat.

8. The system according to claim 7, wherein the activation of the flattening element is such that the distance between the inner walls of said flattened tube is less than about 25 mm.

9. The system according to claim 6, wherein said inner surface comprises a guiding groove.

10. The system according to claim 6, wherein said transparent region comprises at least one optical element selected from a lens, a wedge, a polarizer, an aperture, a filter and a grating.

11. The system according to claim 1, wherein the first flattening element is arranged in an opposing fashion to the second flattening element, and the transparent flexible tube is mounted between the first flattening element and the second flattening element, and at least one of the first flattening element and the second flattening element is a transparent optical element.

12. A method for providing a fluid sample to an optical scanning apparatus, comprising:
arranging a transparent flexible tube in a tube holder,
arranging said tube holder in relation to said optical scanning apparatus,
providing fluid to said tube,
moving at least one of a first flattening element and a second flattening element relative to each other thereby changing said transparent flexible tube from a first state to a second state, wherein at least a first cross sectional dimension of said tube is smaller in the second state than in the first state,
acquiring at least one image of the fluid sample in the transparent flexible tube at least in the second state using said optical scanning apparatus, and
clamping the tube to maintain the fluid sample at a stand still while acquiring the at least one image images of the fluid sample.

13. A method for providing a fluid sample to an optical scanning apparatus, comprising:
arranging a transparent flexible tube in a tube holder,
arranging said tube holder in relation to said optical scanning apparatus,
providing fluid to said tube,
moving at least one of a first flattening element and a second flattening element relative to each other thereby changing said transparent flexible tube from a first state to a second state, wherein at least a first cross sectional dimension of said tube is smaller in the second state than in the first state, and acquiring at least one image from the fluid sample in the transparent flexible tube at least in the second state using said optical scanning apparatus,
acquiring at least one image from said optical scanning apparatus,
determining at least one parameter relating to said fluid sample from said at least one image,
determining a new tube thickness from said at least one parameter, and
moving at least one of said first flattening element and said second flattening element relative to each other thereby changing said transparent flexible tube to a third state based on the new tube thickness.

14. The method according to claim 13, wherein said one or more parameters relates to the concentration of particles in said fluid.

15. The method according to claim 13, wherein said optical apparatus is an optical scanning apparatus adapted to scan an image plane through at least a part of said tube to obtain a plurality of images of the sample arranged therein, and/or to acquire at least one image from said fluid sample in said transparent flexible tube in said first state and/or in said second state, wherein said fluid sample is substantially at stand still.

* * * * *